Figure 1:
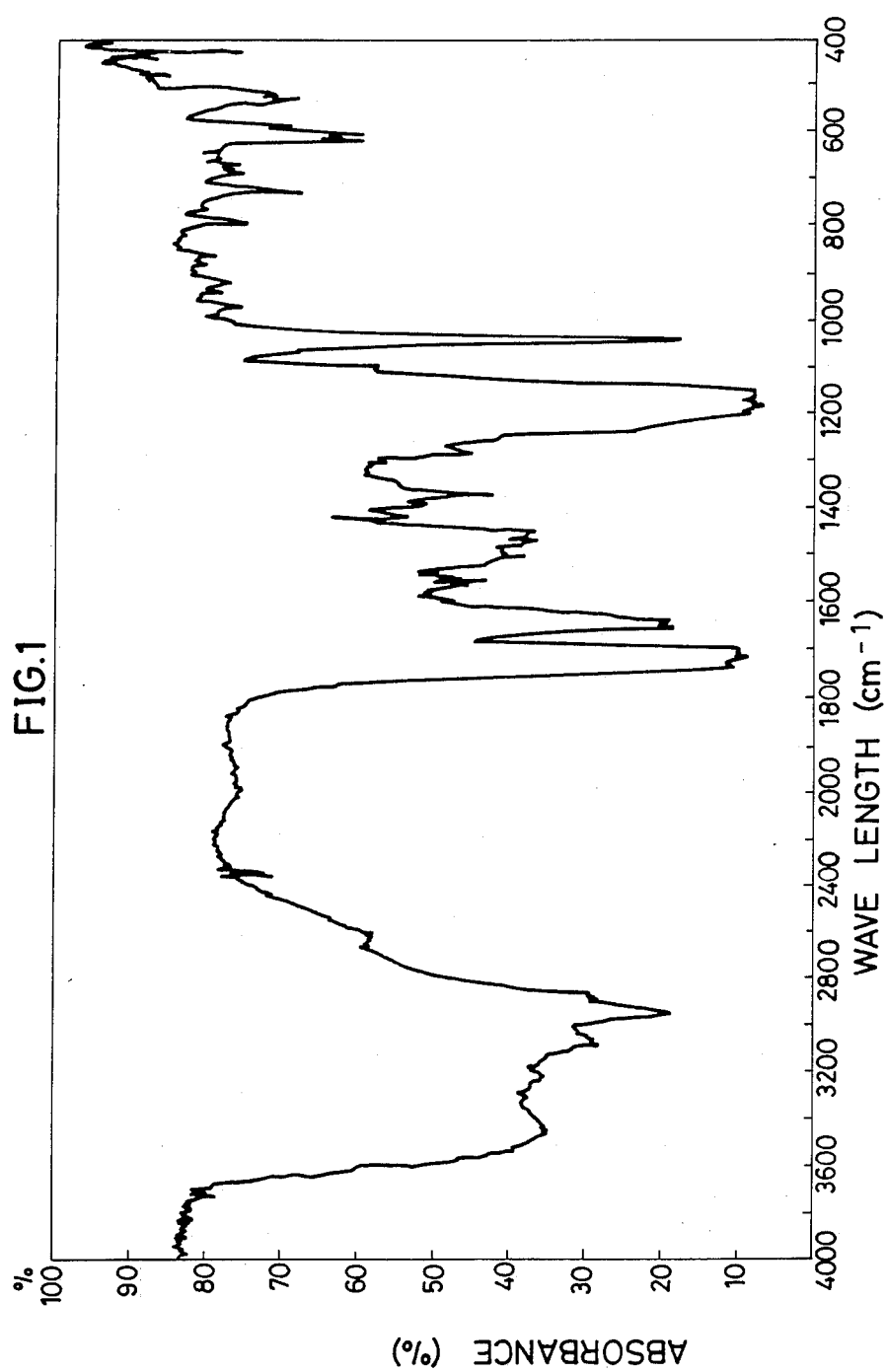

United States Patent [19]
Maeda et al.

[11] Patent Number: 4,868,312
[45] Date of Patent: Sep. 19, 1989

[54] N$^\epsilon$-TRIFLUOROACETYL-L-LYSYL-L-PROLINE.D-10-CAMPHORSULFONIC ACID SALT AND PROCESS FOR PRODUCING THE SAME

[75] Inventors: Sadayuki Maeda, Nara; Usao Nakamura, Sakai; Makoto Sakanaka, Osaka, all of Japan

[73] Assignee: Hamari Chemicals Ltd., Osaka, Japan

[21] Appl. No.: 199,023

[22] Filed: May 26, 1988

[30] Foreign Application Priority Data

May 29, 1987 [JP] Japan .................................. 62-136498

[51] Int. Cl.$^4$ ........................................... C07C 207/08
[52] U.S. Cl. .................................................. 548/535
[58] Field of Search ......................................... 548/533

[56] References Cited

U.S. PATENT DOCUMENTS 4,687,840  8/1987  Pang et al. ...................... 548/533 X
4,720,554  1/1988  Irie et al. ............................ 548/533

Primary Examiner—Joseph Paul Brust
Attorney, Agent, or Firm—Burgess, Ryan & Wayne

[57] ABSTRACT

N$^\epsilon$-Trifluoroacetyl-L-lysyl-L-proline.D-10-camphorsulfonic acid salt is produced in very high purity by reacting N$^\epsilon$-trifluoroacetyl-L-lysyl-L-proline with D-10-camphorsulfonic acid in a suitable solvent, followed by crystallization from the reaction mixture.

The salt is extremely stable at a temperature of working ambience as compared with other salts of N$^\epsilon$-trifluoroacetyl-L-lysyl-L-proline including known dicyclohexylamine salt of the same.

2 Claims, 1 Drawing Sheet

$N^\epsilon$-TRIFLUOROACETYL-L-LYSYL-L-PROLINE.D-10-CAMPHORSULFONIC ACID SALT AND PROCESS FOR PRODUCING THE SAME This invention relates to $N^\epsilon$-Trifluoroacetyl-L-lysyl-L-proline-D-10-camphor sulfonic acid and salts thereof which are important intermediates for the angiotensin converting enzyme inhibitor.

$N^\epsilon$-Trifluoroacetyl-L-lysyl-L-proline (hereinafter may be abbreviated as "$N^\epsilon$-Tfa-Lys-Pro-OH") has been described in Japanese Patent Application of Unexamined Publication No. 36297/1986 (corr. to U.S. patent application Ser. No. 631132, filed on July 16, 1984, now abandoned). According to the patent application, $N^\epsilon$-Tfa-Lys-Pro-OH is an amorphous substance which has been identified as its N,N-dicyclohexylamine salt.

The present inventors, after follow-up test on the method as described in the patent application, found that the objective compound, $N^\epsilon$-Tfa-Lys-Pro-OH, ad its N,N-dicyclohexylamine salt are extremely thermolabile and change readily, even at room temperature, to a condensed compound by intermolecular dehydration as represented by the formula (1) and a compound wherein the trifluoroacetyl is eliminated as represented by the formula (2).

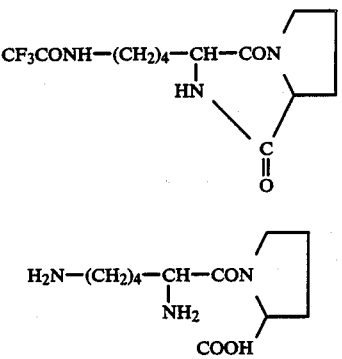

Thermolability is an unfavorable property in view of storage and also presents a fatal or most serious defect in a large scale production.

Accordingly, the present inventors, with a purpose to overcome the above-described defect, synthesized a variety of salts of $N^\epsilon$-Tfa-Lys-Pro-OH and investigated their characteristic properties.

As a result, it was found that methanesulfonic acid, benzenesulfonic acid, p-toluenesulfonic acid, xylenesulfonic acids and naphthalenesulfonic acids can form relatively thermostable salts with $N^\epsilon$-Tfa-Lys-Pro-OH, but the stabilities of the salts are not fully satisfactory from an industrial point of view. In addition, it turned out that the resulting salts all are amorphous substance being difficult to isolate and purify by conventional methods such as crystallization, recrystallization etc., which brings about great difficulty in achieving the salts in allowable quality as a drug intermediate.

Accordingly, the present inventors carried out further intensive studies to research industrially practicable salts, and found that D-10-camphorsulfonic acid salt of $N^\epsilon$-Tfa-Lys-Pro-OH can overcome these defects.

Namely, the present inventors have found that $N^\epsilon$-Tfa-Lys-Pro-OH.D-10-camphorsulfonic acid salt (hereinafter abbreviated as "$N^\epsilon$-Tfa-Lys-Pro-OH.D-CSA salt") is an extremely stable substance at a temperature of normal working ambient, that $N^\epsilon$-Tfa-Lys-Pro-OH.D-CSA salt can be produced by reacting $N^\epsilon$-Tfa-Lys-Pro-OH with D-10-camphorsulfonic acid (hereinafter may be abbreviated as "D-CSA") and that the $N^\epsilon$-Tfa-Lys-Pro-OH.D-CSA salt can be crystallized from a suitable solvent, of which advantage can be taken to easily obtain high purity of $N^\epsilon$-Tfa-Lys-Pro-OH.D-CSA salt in high yields.

Basing on the above findings, the present invention has been established.

The aspects of the invention are directed to $N^\epsilon$-trifluoroacetyl-L-lysyl-L-proline.D-10-camphorsulfonic acid; a process for producing $N^\epsilon$-trifluoroacetyl-L-lysyl-L-proline.D-10-camphorsulfonic acid salt, which comprises reacting $N^\epsilon$-trifluoroacetyl-L-lysyl-L-proline with D-10-camphorsulfonic acid; and a process for producing $N^\epsilon$-trifluoroacetyl-L-lysyl-L-proline.D-10-camphorsulfonic acid salt of high purity, which comprises dissolving $N^\epsilon$-trifluoroacetyl-L-lysyl-L-proline.D-10-camphorsulfonic acid in a solvent and allowing it to crystallize out of the resulting solution.

The $N^\epsilon$-Tfa-Lys-Pro-OH.D-CSA salt can be produced readily by reacting $N^\epsilon$-Tfa-Lys-Pro-OH preferably with an equimolar amount of D-CSA. The reaction is normally carried out in a solvent for allowing the reaction to proceed smoothly. As the solvent, there may be used any solvent which does not interfere with the reaction. As the solvent, there may be exemplified water; an alcohol such as methanol or isopropyl alcohol; a ketone such as acetone or methyl isobutyl ketone; an ester such as methyl acetate or ethyl acetate; an ether such as diethyl ether or tetrahydrofuran; and a mixture of above-mentioned solvents or the like.

The reaction temperature is not limited particularly, but in reactions wherein acetic acid esters or methyl isobutyl ketone and the like being inferior in dissolving $N^\epsilon$-Tfa-Lys-Pro-OH are employed as a solvent, heating at a temperature lower than the boiling point of each solvent often serves to allow the reaction to proceed more speedy.

After completion of the reaction, the solvent is removed from the reaction mixture to thereby give $N^\epsilon$-Tfa-Lys-Pro-OH.D-CSA salt usually in the form of solid substance.

The crude $N^\epsilon$-Tfa-Lys-Pro-OH.D-CSA salt as obtained in this manner can be purified by dissolving it in a solvent and allowing it to crystallize out of the resulting solution.

This property is one of the remarkably excellent characteristic features of $N^\epsilon$-Tfa-Lys-Pro-OH.D-CSA salt.

As the purification procedure to provide $N^\epsilon$-Tfa-Lys-Pro-OH.D-CSA salt in high purity, the difference in solubility in various solvents may be utilized. Namely, various techniques in recrystallization may be applied; for example, the crude product is dissolved under heating in a suitable solvent, after cooling, the product crystallizes from the solution, and the crystals are collected by filtration and dried, thereby $N^\epsilon$-Tfa-Lys-Pro-OH.D-CSA salt can be obtained in high purity. As the solvent, there may be employed a mixture of solvents which consists of a solvent showing enhanced solubility toward the above D-CSA salt and a solvent exhibiting slight solubility toward the salt. Examples of the former solvent include methanol, acetone, etc., while examples of the latter include acetic acid esters, methyl isobutyl ketone and the like. The use of the mixed solvent generally affords favorable results.

The purified product is usually dried under reduced pressure.

N$^\epsilon$-Tfa-Lys-Pro-OH.D-CSA salt can be produced and purified continuously in one step. For example, N$^\epsilon$-Tfa-Lys-Pro-OH and D-CSA are reacted in a suitable solvent such as the solvent being usable for the above-described purification method, to thereby allow N$^\epsilon$-Tfa-Lys-Pro-OH.D-CSA salt of high purity to crystallize out of the reaction mixture directly. In such a case, increased yields can be attained by carrying out the reaction in a solvent under heating at a temperature lower than the boiling point of the solvent and then collecting D-CSA salt which crystallizes out of the reaction mixture after cooling.

As described in the above, different other techniques can be employed as a procedure of allowing the D-CSA salt to crystallize out of the reaction mixture. For example, preferred use is made of the procedure, which comprises carrying out the reaction in a solvent showing enhanced solubility toward both the starting compound and reaction product, such as methanol and acetone, and then mixing the reaction mixture with a solvent exhibiting slight solubility toward them, such as acetic acid esters and methyl isobutyl ketone, to allow N$^\epsilon$-Tfa-Lys-Pro-OH.D-CSA salt of high purity to crystallize out of the reaction mixture.

N$^\epsilon$-Tfa-Lys-Pro-OH.D-CSA salt of this invention shows physicochemical characteristics as described in the following;

(1) Infrared absorption spectrum:
   As is illustrated in FIG. 1
(2) Specific rotation:

$[\alpha]_D^{20} -18.8°$ (H$_2$O, C=2.0)

(3) Elemental analysis:
   As is given in Table 1.

TABLE 1

For $C_{13}H_{20}F_3N_3O_4 \cdot C_{10}H_{16}O_4S$

| | Theoretical, % | Found, % |
|---|---|---|
| C | 48.33 | 47.95 |
| H | 6.35 | 6.40 |
| N | 7.35 | 7.24 |
| F | 9.97 | 9.85 |
| S | 5.61 | 5.57 |

Below described is the stability of N$^\epsilon$-Tfa-Lys-Pro-OH.D-CSA salt.

Free base (lyophilized product) of N$^\epsilon$-Tfa-Lys-Pro-OH, its N,N-dicyclohexylamine salt and D-CSA salt (the compound of this invention) were placed in 1 g portion, and tightly sealed, in individual small glass bottles, followed by storage for 3 weeks in a thermostat at 40° C. to conduct comparative study on thermostability. The results are shown in Table 2. The free base as described above was prepared by allowing an aqueous solution of N$^\epsilon$-Tfa-Lys-Pro-OH.N,N-dicyclohexylamine salt as synthesized in accordance with Examples 1 and 2 of the Japanese Unexamined Published Patent Application No. 36297/1986 to pass through a column of a weakly acidic ion exchange resin on order to absorb dicyclohexylamine and lyophilizing the effluent. HPLC analysis determined that the free base showed a purity of 98.46%. By the same procedure, the purity of the N,N-dicyclohexylamine salt was measured as 98.76%, while the D-CSA salt as prepared in Example 1 was found to show a purity of 99.9%.

As described in the above, N$^\epsilon$-Tfa-Lys-Pro-OH.D-CSA salt of this invention not only exhibits an exceedingly increased level of purity, but also is remarkably improved in thermostability as apparent from Table 2, as compared with the corresponding free base and its dicyclohexylamine salt.

As explained in the above, N$^\epsilon$-Tfa-Lys-Pro-OH.D-CSA salt is an extremely stable substance at a temperature of usual working ambience and can also be allowed to crystallize out of a suitable solvent, enabling N$^\epsilon$-Tfa-Lys-Pro-OH of exceedingly high purity to be produced in the form of D-CSA salt. Furthermore, by selecting a suitable solvent, the reaction of N$^\epsilon$-Tfa-Lys-Pro-OH with D-CSA and crystallization of the reaction product, N$^\epsilon$-Tfa-Lys-Pro-OH.D-CSA salt, can be performed continuously. Thus, exceedingly high purity of N$^\epsilon$-Tfa-Lys-Pro-OH.D-CSA salt can be produced in remarkably efficient manner.

Referring to the drawing, FIG. 1 shows an infrared absorption spectrum of N$^\epsilon$-Tfa-Lys-Pro-OH.D-CSA salt according to present invention.

TABLE 2

Results of comparative study on the thermostability at 40° C. over the 3-week period of N$^\epsilon$—Tfa-Lys-Pro-OH and various salts thereof

| Name of compound | Component | At the time of initiation | 2 days later | 7 days later | 21 days later |
|---|---|---|---|---|---|
| N$^\epsilon$—Tfa-Lys-Pro-OH | N$^\epsilon$—Tfa-Lys-Pro-OH | 98.46% | 97.15% | 90.89% | 64.03% |
| | Dehydration condensed product | 1.02% | 2.32% | 8.55% | 35.43% |
| | Compound having the trifluoroacetyl removed | 0.02% | 0.02% | 0.02% | 0.03% |
| N$^\epsilon$—Tfa-Lys-Pro-OH. N,N—dicyclcohexylamine salt | N$^\epsilon$—Tfa-Lys-Pro-OH | 98.76% | 95.70% | 90.12% | 83.34% |
| | Dehydration condensed product | 0.90% | 3.81% | 9.14% | 15.35% |
| | Compound having the trifluoroacetyl removed | 0.02% | 0.16% | 0.43% | 0.97% |
| N$^\epsilon$—Tfa-Lys-Pro-OH. D-10-camphorsulfonic acid salt | N$^\epsilon$—Tfa-Lys-Pro-OH | 99.9% | 99.9% | 99.9% | 99.9% |
| | Dehydration condensed product | 0% | 0% | 0% | 0% |
| | Compound having the trifluoroacetyl removed | 0% | 0% | 0% | 0% |

Given below are the examples to illustrate this invention in more detail, but this invention is not intended to be limited to them.

REFERENCE EXAMPLE

Synthesis of $N^\epsilon$-trifluoroacetyl-L-lysyl-L-proline $N^\epsilon$-Trifluoroacetyl-L-lysyl-L-proline.N,N-dicyclohexylamine salt (HPLC purity of 98.76%) as synthesized in accordance with the example described in the Japanese Patent Application of Unexamined Publication No. 36297/1986 (corr. to U.S. patent application Ser. No. 631132, filed on July 16, 1984) is dissolved in a small volume of water, adsorbed onto weakly acidic ion exchange resin IRC-84 (H type) and desorbed with water, and the fraction containing $N^\epsilon$-trifluoroacetyl-L-lysyl-L-proline is collected, then decolorized with activated carbon and lyophilized to give the free form of $N^\epsilon$-trifluoroacetyl-L-lysyl-L-prolene as white powder.

This product was found to show 98.46% of purity as determined by HPLC analysis and a specific rotation of $[\alpha]_D^{20}$ $-48.8°$ (H$_2$O, C=1.35).

EXAMPLE 1

Dissolved in 200 ml of methanol are 33.9 g (0.1 mole) of $N^\epsilon$-trifluoroacetyl-L-lysyl-L-proline (98.46% of HPLC purity) and 23.2 g (0.1 mole) of D-10-camphorsulfonic acid, and the methanol is removed under reduced pressure to give $N^\epsilon$-trifluoroacetyl-L-lysyl-L-proline.D-10-camphorsulfonic acid salt quantitatively in the form of white powder.

Subsequently, 57.1 g of the resulting D-10-camphorsulfonic acid salt is dissolved in 230 ml of ethyl acetate containing 7 ml of methanol under heating at 50° C. The solution is cooled gradually and left on standing overnight at room temperature, and the resulting precipitate is recovered by filtration and dried under vacuum at 30° C. to give 53.3 g of $N^\epsilon$-trifluoroacetyl-L-lysyl-L-proline D-10-camphorsulfonic acid salt in the form of white powder. Yield of 93.3%.

This product shows a purity of 99.9% (HPLC) and a specific rotation of $[\alpha]_D^{20}$ $-18.8°$ (H$_2$O, C=2.0).

EXAMPLE 2

Dissolved in 300 ml of ethyl acetate containing 10 ml of methanol are 33.9 g (0.1 mole) of $N^\epsilon$-trifluoroacetyl-L-lysyl-L-proline (98.46% of HPLC purity) and 23.2 g (0.1 mole) of D-10-camphorsulfonic acid, while heating under reflux, and the solution is cooled gradually and left standing overnight at room temperature. The precipitate is collected by filtration and dried under vacuum at 40° C. to give 49.7 g of $N^\epsilon$-trifluoroacetyl-L-lysyl-L-proline.D-10-camphorsulfonic acid salt in the form of white powder. Yield of 87.0%.

This product shows a purity of 99.9% (HPLC) and a specific rotation of $[\alpha]_D^{20}$ $-18.8°$ (H$_2$O, C=2.0).

EXAMPLE 3

Dissolved in 135 ml of ethyl acetate containing 27 ml of acetone are 27.1 g (0.08 mole) of $N^\epsilon$-trifluoroacetyl-L-lysyl-L-proline (98.46% of HPLC purity) and 18.6 g (0.08 mole) of D-10-camphorsulfonic acid, while heating under reflux, and the solution is cooled overnight at 0° to 5° C. The precipitate is collected by filtration and dried under vacuum at 40° C. to give 40.8 g of $N^\epsilon$-trifluoroacetyl-L-lysyl-L-proline.D-10-camphorsulfonic acid salt in the form of white powder. Yield of 89.2%.

This product showed a purity of 99.8% (HPLC) and a specific ratation of $[\alpha]_D^{20}$ $-18.8°$ (H$_2$O, C=2.0).

We claim:

1. $N^\epsilon$-Trifluoroacetyl-L-lysyl-L-proline.D-10-camphorsulfonic acid salt.

2. A salt according to claim 1 wherein the salt shows the specific rotation of $[\alpha]_D^{20}$ $-18.8°$ (H$_2$O, C=2.0).

* * * * *